(12) United States Patent
Thanoo et al.

(10) Patent No.: US 8,329,863 B2
(45) Date of Patent: Dec. 11, 2012

(54) GONADOTROPIN RELEASING HORMONE ANTAGONISTS

(75) Inventors: Bagavathikanun C. Thanoo, Brecksville, OH (US); James Murtagh, Wilmington, NC (US)

(73) Assignee: Oakwood Laboratories, LLC, Oakwood Village, OH (US)

( * ) Notice: Subject to any disclaimer, the term of this patent is extended or adjusted under 35 U.S.C. 154(b) by 1149 days.

(21) Appl. No.: 12/085,496

(22) PCT Filed: Jul. 18, 2005

(86) PCT No.: PCT/US2005/025467
§ 371 (c)(1),
(2), (4) Date: May 21, 2008

(87) PCT Pub. No.: WO2006/010155
PCT Pub. Date: Jan. 26, 2006

(65) Prior Publication Data
US 2009/0105153 A1 Apr. 23, 2009

Related U.S. Application Data

(60) Provisional application No. 60/588,826, filed on Jul. 16, 2004.

(51) Int. Cl.
*A61K 38/04* (2006.01)
*A61K 38/24* (2006.01)
*A61K 38/00* (2006.01)
*A61K 38/09* (2006.01)
*A61K 38/22* (2006.01)
*A61K 51/00* (2006.01)

(52) U.S. Cl. ........ 530/328; 530/313; 530/330; 514/10.6; 514/10.3; 514/10.2; 514/10.1; 514/9.9; 514/9.8; 514/1.1; 424/1.69

(58) Field of Classification Search .................. None
See application file for complete search history.

(56) References Cited

U.S. PATENT DOCUMENTS

| | | | |
|---|---|---|---|
| 4,818,542 A | 4/1989 | DeLuca et al. | |
| 4,935,491 A * | 6/1990 | Folkers et al. | 530/313 |
| 5,296,468 A | 3/1994 | Hoeger et al. | |
| 5,480,969 A * | 1/1996 | Bowers et al. | 530/328 |
| 5,506,207 A | 4/1996 | Rivier et al. | |
| 5,508,383 A * | 4/1996 | Sauer et al. | 530/313 |
| 5,516,887 A | 5/1996 | Deghenghi et al. | |
| 5,656,727 A | 8/1997 | Bowers et al. | |
| 5,945,126 A | 8/1999 | Thanoo et al. | |
| 6,270,802 B1 | 8/2001 | Thanoo et al. | |
| 6,361,798 B1 | 3/2002 | Thanoo et al. | |
| 2005/0042294 A1 | 2/2005 | Thanoo et al. | |

FOREIGN PATENT DOCUMENTS

WO WO 01/10414 A 2/2001

OTHER PUBLICATIONS

Jiang, et al., 2002, "Identification and Determination of GnRH Antagonist Gelling at Injection Site." International Journal of Pharmaceutics, vol. 233, pp. 19-27.
Kostanski, et al., 2000, "Effect of the Current LHRH Antagonist Administration with a LHRH Superagonist in Rats." Pharmaceutical Research, vol. 17, No. 4, pp. 445-450.
Kostanski, et al., 2001, "Evaluation of Orntide Microspheres in a Rat Animal Model and Correlation to In Vitro Release Profile." AAPS Pharm Sci Tech., vol. 1(4) Article 27 (http://pharmscitech.com).
Mann, et al., 1998, "Sexual Maturation in Male Rhesus Monkeys: Importance of Neonatal Testosterone Exposure and Social Rank" Journal of Endocrinology 156: 493-501.
Morales, et al., 2002, "Inhibition of In Vivo and In Vitro Fertilization in Rodents by Gonadotropin-Releasing Hormone Antagonists" Biology of Reproduction 67: 1360-1365.
Herbst, Karen L., 2003, "Gonadotropin-releasing hormone antagonists." Current Opinion in Pharmacology, vol. 3 No. 6, pp. 660-666.

* cited by examiner

*Primary Examiner* — Maury Audet
(74) *Attorney, Agent, or Firm* — Nanda P. B. A. Kumar; Reed Smith LLP (57) ABSTRACT

Antagonistic peptides of GnRH having improved water solubility are disclosed. These peptides are capable of suppressing serum testosterone levels in vivo to chemical castration levels of ≦0.5 ng/ml. Stable, filter sterilizable, non-gelling solutions containing the GnRH antagonists at least at levels typically used in sustained release formulations also are disclosed, as is a method of increasing the solubility of GnRH antagonist in a polymer containing dispersed phase, which method comprises addition of an acid to the dispersed phase.

21 Claims, 8 Drawing Sheets

GONADOTROPIN RELEASING HORMONE ANTAGONISTS

This application is the United States national stage of International Application No. PCT/US2005/025467, filed Jul. 18, 2005, which was published under PCT Article 21 in English as International Publication No. WO 2006/010155, and which claims benefit of U.S. Provisional Application 60/588,826 filed Jul. 16, 2004 and the text of application 60/588,826 is incorporated by reference in its entirety herewith.

FIELD OF THE INVENTION

The present invention relates to antigonadotropic agents for application in hormone-dependent physiological and pathological conditions in mammals. In particular, the present invention relates to synthetic peptides which are antagonists of gonadotropin releasing hormone (GnRH). The present invention also relates to the use of pharmaceutical compositions containing GnRH antagonists in methods for treating conditions arising from gonadotropin stimulated hypersecretion of steroids.

BACKGROUND OF THE INVENTION

Gonadotropin releasing hormone (GnRH) is a peptide hormone synthesized in the hypothalamus and it plays an important role in regulating sex-hormones produced by the pituitary gland. Structurally, GnRH is a decapeptide with the amino acid sequence Pyro-Glu$^1$-His$^2$-Trp$^3$-Ser$^4$-Tyr$^5$-Gly$^6$-Leu$^7$-Arg$^8$-Pro$^9$-Gly$^{10}$-NH$_2$. It is also known in the art as luteinizing hormone releasing hormone (LHRH).

Once GnRH is released from the hypothalamus, it interacts with the surface receptors of pituitary gonadotropes. Once the surface receptors are stimulated, the gonadotropes synthesize and release the so called gonadotropins, luteinizing hormone (LH) and follicle-stimulating hormone (FSH). The significance of these hormones in human reproduction is known. For example, FSH regulates spermatogenesis in males and follicle development in females, and LH regulates gonadal steroid production such as testosterone. Thus, hormone release by the pituitary gland is believed to require prior release of the GnRH decapeptide by the hypothalamus. Since these findings, GnRH analogs that are antagonistic to the normal function of GnRH decapeptide, also known as GnRH antagonists, have been used to suppress secretion of gonadotropins in mammals including humans. Essentially, GnRH antagonists act to lower the circulating levels of FSH and LH.

Of late, a number of GnRH antagonists have been developed for clinical use as agents for controlling testosterone secretion or ovulatory activity and for treating a variety of other hormone-sensitive human conditions such as prostate cancer and endometriosis. The antagonists are also being used for other gynecological purposes particularly to suppress the LH-surge in assisted conception. In terms of action, the GnRH antagonists have been reported to block the access of native GnRH peptides to GnRH receptors and thus suppress gonadotropin production.

In the search for improved GnRH antagonists, the focus has been on reducing the potential for histamine release, maintaining or increasing gonadotropin suppressive potency and increasing water solubility. For example, U.S. Pat. Nos. 5,656,727, 5,516,887, 5,506,207, 5,480,969 and 5,296,468 disclose the design and synthesis of a number of GnRH antagonists. Despite the attractive properties of a number of GnRH antagonists described in the above patents, the search for further improved GnRH antagonists continues. Orntide (DNal$^1$, DpCIPhe$^2$, D3Pal$^3$ Ser$^4$, PicLys$^5$, D(6ANic)Orn$^6$, Leu$^7$, IprLys$^8$, Pro$^9$, DAla$^{10}$-NH$_2$ (U.S. Pat. Nos. 5,480,969 and 5,656,727; Janecka, et. al., J. Med. Chem., 1994, 37: 2238-2241), an antagonist of GnRH, reportedly is one of the most effective GnRH antagonists developed to date (Jiang et al., Intl. J. Pharmaceutics, 2002, 233: 19-27). It has been reported to have high antigonadotropic potency and low histamine release and relatively favorable water solubility. Still further improved GnRH antagonists, particularly those which exhibit higher water solubility than orntide in a formulation having a pH ranging from about 5 to about 7, more preferably at pH 7.4, and have favorable biological effectiveness would be desirable.

SUMMARY OF THE INVENTION

In the present invention, GnRH antagonists possessing unique and favorable pharmacological properties have been found. These properties make them ideal candidates for the management of sex steroid-dependent pathologies, particularly those pathologies requiring long-term suppression of the gonadotropic axis. For example, in the present invention, it has been found that certain modifications to orntide, particularly to the residue in position 5, result in GnRH antagonists exhibiting higher water solubility than orntide at normal physiological pH while having other favorable properties such as antigonadotropic potency. In general aspects of the invention, GnRH antagonists having the formula: AcDNal$^1$, DpCIPhe$^2$, D3Pal$^3$ Ser$^4$, NicLys$^5$, D(6ANic)Orn$^6$, Pro$^9$, DAla$^{10}$NH$_2$, their closely related analogs and pharmaceutically acceptable salts thereof are found to have improved water solubility and other favorable pharmaceutical properties.

In an aspect of the invention, a method of controlling gonadotropin levels in a mammal is provided. The method involves delivery of or administering a GnRH antagonist in an amount and frequency effective to substantially suppress endogenous gonadotropin levels in the mammal. Alternatively or in addition to the above, the method involves administering a GnRH antagonist in a frequency (for example more than once per day) effective to substantially suppress endogenous gonadotropin levels in the mammal. In mammals suffering from hypersecretion of gonadotropins, GnRH antagonist of the present invention is administered in an amount and frequency effective to maintain gonadotropins at a desired level in those mammals. This method is especially useful for treating mammals who suffer from gonadotropin related disorders such as prostate and ovarian disorders or overproduction of androgens in females, or abnormally high levels of LH or FSH wherein it is desired to reduce such high levels to normal or approximately normal levels. By practicing the methods of the present invention, gonadotropin or steroid level in a mammal can be maintained for a defined treatment period at a desired level in a mammal and can be reverted back to normal levels after cessation of the treatment.

In another aspect of the invention, a method of suppressing testosterone levels in mammals including humans for a defined treatment period is provided. In this method, an amount of a pharmaceutical composition containing an effective amount of a GnRH antagonist of the present invention (for example either AcDNal$^1$, DpCIPhe$^2$, D3Pal$^3$ Ser, NicLys$^5$, D(6ANic)Orn$^6$, Leu$^7$, IprLys$^8$, Pro$^9$, DAla$^{10}$NH$_2$ or AcDNal$^1$, DpCIPhe$^2$, D3Pal$^3$ Ser$^4$, NicLys$^5$, D(6ANic)Orn$^6$, Val$^7$, IprLys$^8$ (or Arg$^8$), Pro$^9$, DAla$^{10}$NH$_2$) and a suitable carrier or diluent is administered. The amount of a pharmaceutical composition administered is such that it effects a substantial decrease in testosterone levels.

In still another aspect of the invention, a method for diagnosing a condition involving tumor cell proliferation and/or excess hormonal secretion, which condition is directly or indirectly induced by GnRH, is provided. In this method, a GnRH antagonist of the present invention is administered either to the appropriate in vitro cell cultures or in vivo and hormonal secretion, steroid level and/or tumor cell proliferation is monitored at various intervals.

The present invention also discloses other aspects related to a composition for a dispersed phase formulation or a microsphere containing a gonadotropin releasing hormone antagonist having the formula: $AcDNal^1$, $DpClPhe^2$, $D3Pal^3$, $Ser^4$, $NicLys^5$, $D(6ANic)Orn^6$, $Leu^7$, $IprLys^8$, $Pro^9$, $DAla^{10}NH_2$. In an embodiment, a composition for a dispersed phase formulation contains or consists essentially of a gonadotropin releasing hormone (GnRH) antagonist having the formula: $AcDNal^1$, $DpClPhe^2$, $D3Pal^3$, $Ser^4$, $NicLys^5$, $D(6ANic)Orn^6$, $Leu^7$, $IprLys^8$, $Pro^9$, $DAla^{10}NH_2$ and an acid additive. The GnRH analog is preferably a freeze-dried GnRH antagonist and the acid additive is an organic acid or an inorganic acid additive or both organic and inorganic acid. It is preferred that the organic or inorganic acid additive has a pKa of 5.0 or lower. The organic acid additive can be at least one of glacial acetic acid, lactic acid, glycolic acid, glyceric acid, benzoic acid, propanoic acid, methane sulfonic acid, and mesitylic acid. The preferred inorganic acid additive is HCl although other inorganic acids that has the desired pKa value can also be used. The composition optionally has a biocompatible and biodegradable polymer such as, for example, a homopolymer of lactic acid or a copolymer of lactic acid and glycolic acid.

Preferred compositions for microspheres are those containing a GnRH antagonist having or consisting essentially of the formula: $AcDNal^1$, $DpClPhe^2$, $D3Pal^3$, $Ser^4$, $NicLys^5$, $D(6ANic)Orn^6$, $Pro^9$, $DAla^{10}NH_2$. In addition, the microsphere compositions have a polymer with a given acid number, which number preferably is at least 5 in case the polymer is composed of 100% lactide or at least 15 in case the polymer is composed of 50% lactide and 50% glycolide, or is between 10 and 40. The polymer may contain at least 50% lactide or 100% lactide. The microsphere composition may optionally have one or more organic acids such as, for example, acetic acid, lactic acid, glycolic acid, butyric acid, valeric acid, decanoic acid, stearic acid or citric acid added to the composition. The amount of the antagonist in the compositions is not more than 40 percent by weight relative to the polymer matrix. The amount of organic acid added is such that it is present at a level of about 5% to about 50% by weight.

The microsphere preparation involves the use of a dispersed phase and a continuous phase. The selected continuous phase is one in which the dispersed phase will form an emulsion. The dispersed phase is formed by mixing a first organic solution and a second organic solution. The first organic solution formed by dissolving an amount of a polymer in an amount of the first organic solvent (e.g., dichloromethane or chloroform), the first organic solvent being immiscible with water. The second organic solution formed by adding an amount of a second organic solvent, with which the first organic solvent is miscible, to a GnRH antagonist of the invention, for example, an antagonist having the formula $AcDNal^1$, $DpClPhe^2$, $D3Pal^3$, $Ser^4$, $NicLys^5$, $D(6ANic)Orn^6$, $Leu^7$, $IprLys^8$, $Pro^9$, $DAla^{10}NH_2$ or to a solution formed by dissolving the antagonist of GnRH in a sufficient amount of an acid additive and, optionally, by adding an amount of the first organic solvent. The acid additive may be any organic acid or an inorganic acid or their combination but the selected acid or the combination preferably has a pKa of 5.0 or lower. For example the selected acid may be at least one of glacial acetic acid, lactic acid, glycolic acid, glyceric acid, benzoic acid, propanoic acid, methane sulfonic acid, mesitylic acid and HCl. The dispersed phase is then emulsified in the continuous phase to form microspheres. From the microspheres so formed, the first and second organic solvents are removed to recover the microspheres substantially free, if not completely free, of the organic solvents. The GnRH antagonist used in the microspheres may be one that is freeze-dried.

The present invention also discloses methods for increasing the solubility of a GnRH antagonist having the formula: $AcDNal^1$, $DpClPhe^2$, $D3Pal^3$, $Ser^4$, $NicLys^5$, $D(6ANic)Orn^6$, $Pro^9$, $DAla^{10}NH_2$ in a polymer containing dispersed phase. In an embodiment of the present invention, a method of increasing the solubility of a GnRH antagonist having the formula: $AcDNal^1$, $DpClPhe^2$, $D3Pal^3$ $Ser^4$, $NicLys^5$, $D(6ANic)Orn^6$, $Leu^7$, $IprLys^8$, $Pro^9$, $DAla^{10}NH_2$ in a polymer containing dispersed phase involves all or few of the following various steps: dispensing the GnRH antagonist (whether freeze-dried or not) into a container, adding a first organic solvent to the GnRH antagonist to form a first organic mixture, dissolving an amount of a polymer in a second organic solvent to form a second organic mixture; and mixing the first and second organic mixtures to form the dispersed phase. The method may further involve heating the dispersed phase to 40 C or a temperature sufficient to prevent gelling of the dispersed phase, if necessary. The method may optionally include a step of adding an amount of an acid additive to the dispersed phase. The amount of the acid additive in the dispersed phase may be such that it is sufficient to increase the solubility of the GnRH antagonist in the dispersed phase without affecting release characteristics of any microspheres prepared therefrom. The first organic solvent may be any of or at least one of methanol, ethanol, dimethyl sulfoxide, dimethyl formamide, dimethyl acetamide, N-methylpyrrolidone, dioxane, tetrahydrofuran, methylene chloride, ethylene chloride, carbon tetrachloride, chloroform, diethyl ether, methyl ethyl ether, hexane, cyclohexane, benzene, acetone, ethyl lactate, or ethyl acetate.

In another embodiment of the present invention, a method of increasing the solubility of a GnRH antagonist (freeze-dried), having the formula: $AcDNal^1$, $DpClPhe^2$, $D3Pal^3$ $Ser^4$, $NicLys^5$, $D(6ANic)Orn^6$, $Leu^7$, $IprLys^8$, $Pro^9$, $DAla^{10}NH_2$, in a polymer containing dispersed phase involves all or few of the following various steps: dissolving the freeze-dried antagonist of GnRH in a sufficient amount of an acid additive to form a solution, adding an amount of an organic solvent to the solution to form a first organic solution, dissolving an amount of a polymer in an amount of the organic solvent to form a second organic solution, and mixing the first and second organic solutions to form a dispersed phase. The method includes an optional step of adding at least one of methanol, ethanol, dimethyl sulfoxide (DMSO), dimethyl formamide, dimethyl acetamide, dioxane, tetrahydrofuran (THF), N-methylpyrrolidone, ethylene chloride, carbon tetrachloride, chloroform, diethyl ether, methyl ethyl ether, hexane, cyclohexane, benzene, acetone, ethyl lactate, or ethyl acetate to the solution before the step of adding the organic solvent.

The acid additive used (preferably having a pKa of 5.0 or lower) in the methods of increasing the solubility of a selected gonadotropin releasing hormone (GnRH) of the present invention may be at least one of glacial acetic acid, lactic acid, glycolic acid, glyceric acid, benzoic acid, propanoic acid, methane sulfonic acid, mesitylic acid and HCl.

BRIEF DESCRIPTION OF THE DRAWINGS

FIG. 3 shows mean serum testosterone levels in control rats (i.e., after vehicle only administration) for three weeks. Testosterone levels after water for injection (WFI) administration at a dose of 0.3 ml/rat in week 1 (3A), in week 2 (3B) and in week 3 (3C).

DETAILED DESCRIPTION OF THE INVENTION

The novel pharmaceutically active chemical agents of the present invention are gonadotropin releasing hormone (GnRH) antagonistic analogs(GnRH antagonists). These antagonistic analogs are believed to be effective in regulating internal testosterone levels in animals and treating a variety of the hormone-sensitive human disease states. The antagonists are peptidic compounds and are preferably made of 10 amino acids. Both the N and C terminals of antagonists preferably are blocked or protected from enzyme degradation so that they exist neither as free acid nor as base. Modifications at the N-terminus include N-acylation, N-formylation, or use of a cyclized amino acid such as pyroglutamate. The C-terminal can be protected by use of an amide or ethylamide instead of a carboxylic acid. The amino acids may also be modified, i.e., use of D-instead of the natural L-amino acids are preferred.

The GnRH antagonists of the present invention have the general formula AcDNal$^1$, DpClPhe$^2$, D3Pal$^3$, Ser$^4$, NicLys$^5$, D(6ANic)Orn$^6$, Pro$^9$, DAla$^{10}$NH$_2$. The —NH$_2$ in the general formula indicates that the C-terminus is an amide rather than a free carboxylic acid. Of the 10 amino acids in the general formula, the amino acids in positions 7 and 8 have not been shown because at these two positions various equivalent amino acid residues can be used. Specifically, either Leu or Val can be used in position 7, with Leu being a preferred amino acid. Either IprLys or Arg can be used in position 8, while IprLys being a preferred amino acid. Substitution of such equivalent residues in positions 7 and 8 is not believed to significantly alter the biological activity of GnRH antagonists of the present invention.

In a preferred embodiment of the present invention, a GnRH antagonist having the following formula is used: AcD-Nal$^1$, DpClPhe$^2$, D3Pal$^3$ Ser$^4$, NicLys$^5$, D(6ANic)Orn$^6$, Leu$^7$, IprLys$^8$, Pro$^9$, DAla$^{10}$NH$_2$. In a still preferred embodiment of the present invention, a GnRH antagonist consisting essentially of the following formula is used: AcDNal$^1$, DpCl-Phe$^2$, D3Pal$^3$ Ser$^4$, NicLys$^5$, D(6ANic)Orn$^6$, Leu$^7$, IprLys$^8$, Pro$^9$, DAla$^{10}$NH$_2$. This GnRH antagonist is structurally similar to the prior art known orntide except that the antagonist has a modified lysine residue in position 5. Orntide has picolinoyllysine in position 5. The antagonist of the present invention has a nicotinoyl substitution on the lysine in position 5. This modification causes the GnRH antagonist to be more polar and thus increases its solubility in water as compared to that of orntide. Solubility determinations are within the purview of those skilled in the art. For example, this can be done by measuring retention time during high pressure liquid chromatography (HPLC) or via a octanol-water partitioning study. Further, this modification is not believed to significantly alter the duration of testosterone suppression or the potential for histamine release by the GnRH antagonist.

The selection of a given peptidic GnRH antagonist to prepare a subcutaneous depot may depend on its propensity to form gels, which propensity could be higher in the subcutaneous environment. The prior art reports that gel formation is dependent on concentration and/or water solubility of a given peptidic GnRH antagonist and increasing the concentration of the antagonist beyond a certain point may affect its bioavailability due to gel formation. In the case of the prior art known orntide acetate, a peptidic GnRH antagonist, for example, the present inventors have found that it is soluble in aqueous media only at concentrations less than 5 mg/mL even at a pH lower than 5. Further, it tends to gel even at that low concentration and whereas the desired concentration of orntide in a formulation for microspheres is at least 100 mg/mL. Also, it has been reported to exhibit concentration dependent gelling at the point of injection at levels exceeding a daily dose of 100 µg/kg bodyweight. (Jiang et al., 2002, Intl J of Pharmaceutics, 233: 19-27).

By using the antagonists of the present invention, the risk of gelling or precipitation upon subcutaneous injection can be lowered because of the improved water solubility of these antagonists. Further, as a result of this advantageous property, it is now anticipated that the daily dose of the GnRH antagonists such as the one shown in FIG. 1, can be several fold more than that of orntide acetate should that be desired. Furthermore, the GnRH antagonists disclosed herein can also be advantageously used in situations where it is desirable to administer a given GnRH antagonist over prolonged periods of time. For example, treatment of prostate cancer may require extended suppression of testosterone to castration levels (i.e., ≦0.5 ng/ml) for periods of few weeks to one year. Because of the superior solubility of GnRH antagonists of the present invention, their bioavailability from the subcutaneous depot may be less dependent on concentration than the bioavailability of the prior art known GnRH antagonists having limited water solubility. As a result, a single or fewer injections of GnRH antagonist(s) of the present invention may be sufficient to achieve the desired LH and testosterone suppression. If necessary, the dose and concentration of the antagonist(s) disclosed herein may be increased so as to realize a marked increase in duration of LH and testosterone suppression. These and other attributes render the GnRH antagonists of the present invention particularly suitable for making therapeutic or protective pharmaceutical compositions for administration by subcutaneous injection compared to orntide or other prior art known GnRH antagonists of generally comparable biological efficacy.

Accordingly, in another aspect, the present invention provides methods for suppressing the secretion of gonadotropins or steroids in a mammal by administering an effective amount of a GnRH antagonist of the present invention with a pharmaceutically acceptable carrier and/or diluent. It includes methods for treatment of hormone related or steroid-dependent pathologies.

As a result of extensive research and clinical testing data already generated for a number of GnRH analogs (e.g. Ganirelix and Cetrorelix), it is within the purview of one skilled in the art to determine how to use the compounds of the present invention as, for example, testosterone suppressing or anti-ovulatory agents. It is believed that the treatment of patients including humans with GnRH antagonists of the present invention can be generally carried out in the same manner using known clinical treatment procedures. In general, the GnRH antagonists are provided in suitable carriers and administered in a dosage effective to suppress gonadotropin levels or steroids in the patient. Various GnRH antagonist preparations and dosages are described further herein. See also, U.S. Pat. Nos. 5,480,969 and 5,656,727; Morales et al., 2002, Biology of Reproduction 67: 1360-1365; Mann et al., 1998, Journal of Endocrinology 156: 493-501; Kostanski et. al., 2000, AAPS PharmSciTech, 1 (4) article 27, the contents of which are incorporated herein by reference).

The GnRH antagonists of the present invention can often be administered in the form of pharmaceutically acceptable nontoxic salts, the salt of acetate being a preferred salt form. The pharmaceutical compositions can contain an effective amount of a given GnRH antagonist in conjunction with a conventional pharmaceutically acceptable carrier. The composition can be in the form of an isotonic solution. A suitable buffer solution such as acetate, citrate or phosphate buffer may be used.

In general, the amount of a GnRH antagonist in the composition may be selected according to known principles of pharmacy. An effective amount of a GnRH antagonist as pharmaceutical ingredient is specifically contemplated. By the term "effective amount," it is understood that with respect to, for example, pharmaceuticals, a "pharmaceutically effective amount" is contemplated. A "pharmaceutically effective amount" is the amount or quantity of a drug or pharmaceutically active substance which is sufficient to elicit the required or desired therapeutic response, or the amount which is sufficient to elicit an appreciable biological response when administered to a patient.

The composition containing a GnRH antagonist of the present invention can be administered to mammals subcutaneously, intramuscularly, intravenously, intranasally, intravaginally or intrarectally to achieve the desired effects such as applications calling for reversible suppression of gonadal activity, in particular reversible suppression of testosterones. Effective dosages can vary with the form of administration and the particular species of mammal being treated. While the prior art known orntide acetate has low water solubility (at concentrations less than 5 mg/mL) at a pH of 5, the GnRH antagonists of the present invention have good solubility at 5 mg/mL, 10 mg/mL, 20 mg/mL, 30 mg/mL and even as high as 50 mg/mL and at pH of about 4.0-5.4. Thus, the GnRH antagonists of the present invention, may suitably be used as 1-50 mg/mL solutions at a pH of about 5. These GnRH antagonists are well-tolerated in vivo.

Usually, the dosage can be from about 90 µg to about 2.5 mg of the GnRH antagonist per kilogram of the body weight of the animal host when given subcutaneously. An example of one typical dosage form is a sterile water or buffer solution at a pH of about 5 containing the GnRH antagonist, which solution is administered subcutaneously to provide a dose in the range of about 0.09 to 2.5 mg/kg of body weight per day.

In another aspect of the invention, sustained release formulations, microsphere and microcapsule formulations, formed from various natural and synthetic polymers and resins as delivery vehicles for the various GnRH antagonists of the present invention are contemplated. Both microspheres and microcapsules contain a matrix (e.g., polymer matrix) in which a drug is dispersed, entrapped, or encapsulated. Microspheres are generally solid polymeric spheres in which a drug is dispersed, entrapped, or encapsulated. Microcapsules are those having an outer polymer shell surrounding a core of active agent(s), in this case, GnRH antagonists of the present invention. The sustained release formulation in its broadest possible sense means a formulation of GnRH antagonists of the present invention resulting in the release of the GnRH antagonist(s) for a sustained or extended period of time or at least for a period of time which is longer than if the GnRH antagonists were made available in vivo in the conventional form without a matrix, i.e., in an unformulated state. Optionally, the release of the GnRH antagonist(s) from these formulations occurs at a constant rate and/or a continuous concentration for a given period. Suitable sustained release formulations may range from 1-day release formulation to six-month release formulation or more as may be determined by one skilled in the art depending on the type of clinical application. Preferred release formulations are 1-month, 3-month and 6-month release formulations. One skilled in the art would know how to prepare various release forms by manipulating the matrix composition.

Microspheres, where the active agent is essentially dispersed, entrapped or encapsulated in a matrix, typically in a polymer matrix, are attractive delivery vehicles because of their potential to provide sustained or delayed release of drugs. Such formulations usually require high levels of the analogs dissolved in small volumes of water or some other suitable solvent(s). The levels of GnRH analogs that are typically used in sustained release formulations range from 50 mg/mL to 100 mg/mL or higher. The relatively low solubility of the prior art GnRH analogs and their concentration-dependent propensity to form gels in aqueous or other solvents greatly limit their use in microsphere formulations. Further, the gelling solution poses a problem for sterile filtration for aseptic manufacturing of the microsphere formulations. In that respect, the GnRH antagonists of the present invention are particularly suitable for use in sustained release formulations, particularly for preparing sterile sustained release formulations by filter sterilizing the solutions of the antagonist and the polymer matrix (either separately or as a combined solution) rather than resort to other less attractive sterilization techniques such as heat, steam and gamma irradiation. Methods for preparing the dispersed phase formulations and microspheres are well known to those skilled in the art. See, for example, the U.S. Pat. Nos. 5,945,126; 6,361,798; 6,270, 802; and 4,818,542, the contents of which are incorporated herein by reference.

The polymer solutions or dispersed phase formulations prepared according to the present invention are suitable for making various sustained release forms such implants or microspheres or microparticles or such others by techniques known to those skilled in the art. These include spray-drying, vacuum-drying, formation of emulsion and solvent evaporation or solvent extraction and spray-freezing. Thus, despite the use of the phrase "dispersed phase" throughout the description herein, the suitability of the formulations is not in any way limited only to dispersal in another phase.

Methods for preparing microspheres, by emulsification process, typically involve the preparation of at least one dispersed phase and a continuous phase. See, for example, the U.S. Pat. Nos. 5,945,126. The dispersed phase typically includes the active agent and polymer material dissolved in solvents. The dispersed phase, upon addition to the continuous phase, forms microspheres in an emulsification process. The polymer in the formulation, which typically serves as a matrix for the active agent (e.g., a GnRH antagonist of the present invention) is preferably biodegradable and biocompatible. Preferred examples of polymer matrix materials lactides and glycolides including poly(glycolic acid), poly(d,l-lactic acid), poly(l-lactic acid), poly(-lactide-co-glycolide), poly(dl-lactide-co-glycolide), poly(l-lactide-co-dl-lactide), other homopolymers or copolymers of the glycolic and lactic acids, and the like. Various polymers have been used in microsphere formulations. See, for example, the U.S. Pat. Nos. 6,361,798, 5,945,126 and 4,818,542.

In a typical practice, the polymer, a selected GnRH antagonist and solvent or solvents are combined to form the dispersed phase. It is preferred that the dispersed phase is a true, homogeneous solution which may be prepared by mixing the polymer, solvent and the selected GnRH antagonist together to form a solution. Alternatively, separate solutions of polymer and the selected GnRH antagonist can be prepared, each in its own solvent, and subsequently mixed to form the dispersed phase solution. Solvents suitable for the preferred poly(lactic) or poly(lactide-co-glycolide) polymers include methylene chloride, chloroform, ethyl acetate, substituted pyrrolidone and the like. The kind of solvent used for preparing the polymer solution can be the same as or different from that used for preparing GnRH antagonist solution.

In some embodiments, the dispersed phase may be formed as an emulsion. For example, when a given GnRH antagonist is dissolved in a suitable solvent, the resulting solution may be completely immiscible with a solution of the polymer and a particular polymer solvent. In order to provide a relatively homogeneous dispersed phase in which the GnRH antagonist and polymer are relatively uniformly interspersed, the GnRH antagonist and its solvent may be emulsified with the polymer and polymer solvent to form a dispersed phase emulsion using known surfactants. Upon introduction of the dispersed phase into the continuous phase, a water-oil-water (W/O/W) emulsion is formed. In still other systems, the dispersed phase can be prepared by forming a direct suspension of the GnRH antagonist in a polymer solution.

The solvent for dissolving polymer and/or a GnRH analog can be the same as or different from that which is typically used in preparing dispersed phase formulations. Typical solvents include, but are not limited to, water, methanol, ethanol, dimethyl sulfoxide (DMSO), dimethyl formamide, dimethyl acetamide, dioxane, tetrahydrofuran (TBF), methylene chloride, ethylene chloride, carbon tetrachloride, chloroform, diethyl ether, methyl ethyl ether, hexane, cyclohexane, benzene, acetone or ethyl acetate.

In some embodiments, a microsphere formulation according to the present invention can contain a desired level of one or more GnRH antagonists of the present invention. The desired concentrations or levels of the GnRH antagonist(s) in a formulation for microspheres can be at least about 25 mg/mL, more preferably at least about 50 mg/mL, still more preferably at least about 100 mg/mL. Given the high solubility of the GnRH antagonists of the present invention, it should be possible to obtain stable solutions containing the antagonists at least at levels typically used in sustained release formulations without the associated solubility and/or gelling problems. The amounts of the GnRH antagonists of the present invention relative to the polymer matrix can be from about 1-40% by weight, preferably from about 5-20% by weight.

Figure 1:
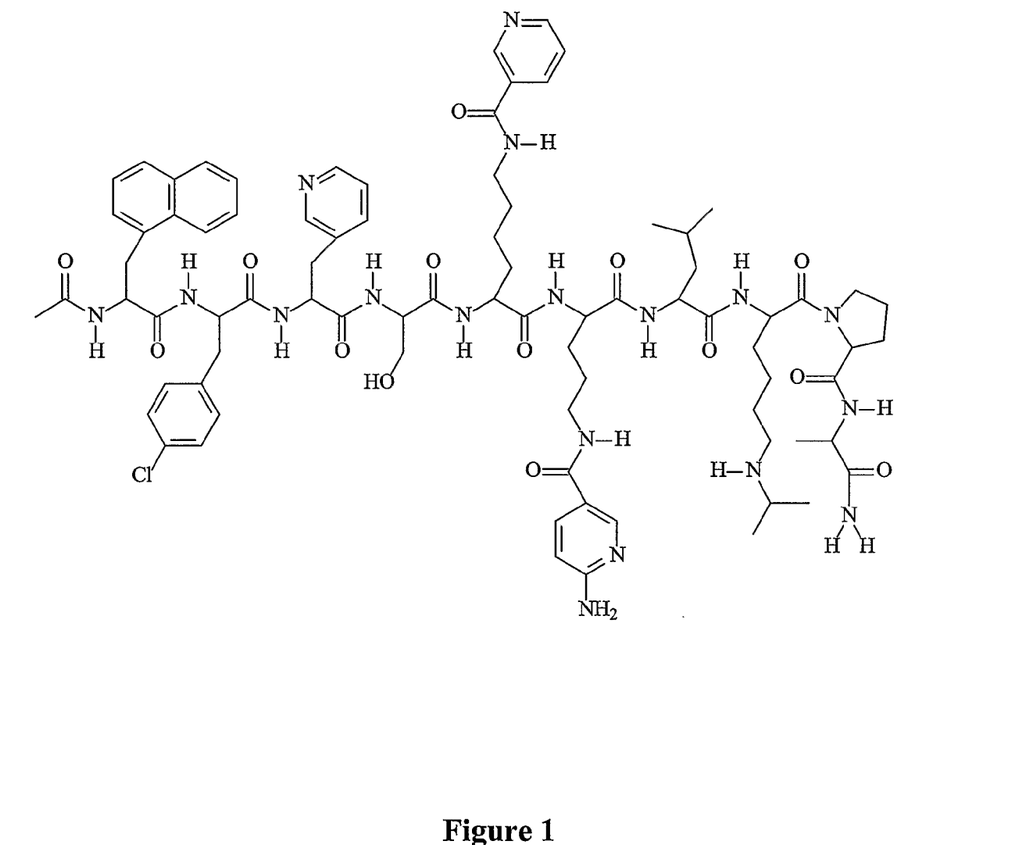
FIG. 1 shows structure of one embodiment of the instant GnRH antagonistic analog.

In an exemplary embodiment, microspheres containing GnRH antagonist having a chemical structure shown in FIG. 1 can be prepared by emulsion and solvent extraction process as follows: About 200 mg of the GnRH antagonist is dissolved in either 2.0 g of methanol. About 3.0 g of a polymer (e.g., RG503H, Lot #290103 from Boehringer Ingelheim) in about 10 g of dichloromethane. The two solutions are mixed to form a polymer solution containing the GnRH antagonist. Microsphere suspension is then formed by dispersing the polymer solution in a suitable continuous phase (e.g., an aqueous solution containing 0.35% (wt/vol.) polyvinyl alcohol) using a homogenizer such as a Silverson Homogenizer (Silverson Machines, Waterside UK) at about 5000 RPM. The microsphere suspension thus formed is transferred to a solvent removal vessel to remove the organic solvents completely or substantially from the suspension. The suspension is then filtered, washed and dried overnight at ambient temperature. The microsphere preparation by emulsion and solvent extraction process is known to one skilled in the art.

To the extent the amount of GnRH antagonist(s) to achieve a desired concentration is no longer soluble in solvent(s) used for preparing a liquid composition or dispersed phase, or the resulting solution is unstable and gels due to the level of antagonist present in the solution, the present invention contemplates unique approaches to address such issues. The unique approaches disclosed herein can be used to achieve the desired solubility as well as stability against gelling. For example, one approach is to use a solution of freeze-dried GnRH antagonist and a non-acid organic solvent in preparing a dispersed phase. The stability against gelling may also be improved by adding small amount of an organic or an inorganic acid, before adding the non-acid organic solvent, to the freeze-dried GnRH antagonist.

More particularly, in one embodiment, the present invention provides GnRH antagonist compositions that exhibit resistance against gelling and are filter sterilizable. The composition is typically a dispersed phase formulation useful for fabricating microspheres. The composition comprises a freeze-dried GnRH antagonist which is preferably obtained from a solution made of a GnRH antagonist and at least one organic solvent. Preferred solvents are selected from the group consisting of methanol, ethanol, dimethyl sulfoxide (DMSO), dimethyl formamide, dimethyl acetamide, dioxane, tetrahydrofuran (THF), methylene chloride, ethylene chloride, carbon tetrachloride, chlorofomm, diethyl ether, methyl ethyl ether, hexane, cyclohexane, benzene, acetone and ethyl acetate. In addition to the freeze-dried GnRH antagonist, the composition may also comprise an organic or an inorganic acid. Examples of organic solvents which could be freeze dried under normal freeze drying cycle are, tert-butanol (TBA) and cyclohexane. For example, 200 mg/mL solution of the antagonist may be made in TBA-water mixture (e.g., 34% TBA and 66% water). To this sample, a sufficient amount of glacial acetic acid (about 3%) may also be added. The solution is then freeze dried. The freezing is carried out, for example, at −50° C. for 2 hours. An exemplary drying cycle can be to ramp from −50° C. to 10° C. over 20 hour period followed by ramp from 10° C. to 25° C. over 20 hour period followed by terminal drying at 25° C. for approximately 10 hours.

In another aspect of the invention, a method of increasing solubility of a desired level of a GnRH antagonist in a polymer containing dispersed phase is provided. The method includes adding an effective amount of a suitable organic solvent to the desired amount of freeze dried GnRH antagonist so as to dissolve the analog completely or as much as possible. Separately, an amount of a polymer in another organic solvent is dissolved and then the antagonist containing portion is mixed with the polymer containing portion to form the dispersed phase. An effective amount of a suitable acid additive may optionally be added to the dispersed phase to increase the solubility, if that is necessary. The amount of the acid additive in the dispersed phase is such that it is just sufficient to increase the solubility of the desired amount of the GnRH antagonist in the dispersed phase. In a preferred embodiment, the amount of acid should be high enough to achieve solubility, and should not be so high that the microsphere could not be formed by O/W (oil in water) or O/O (oil in oil) process. In one preferred embodiment, the amount of acid in the dispersed phase (DP) can be at or less than 50% by weight.

Another method of increasing solubility of a high amount of a freeze-dried antagonist of GnRH in a polymer containing dispersed phase is also provided. According to this method, a desired amount of the freeze-dried antagonist of GnRH is dissolved in a sufficient amount of an acid additive to form a solution, followed by the addition of one or more solvents. For example, a suitable solvent could be a solvent for the polymer, such as dimethyl sulfoxide (DMSO), dimethyl formamide, dimethyl acetamide, dioxane, tetrahydrofuran (THF), methylene chloride, ethylene chloride, carbon tetrachloride, chloroform, ethyl acetate, acetone, ethyl methyl ketone or a non-solvent for the polymer such as methanol, ethanol, cyclohexane, etc. If the added solvent is a non-solvent for the polymer, then the added solvent is limited to the quantity such that the polymer will stay in solution in the final dispersed phase.

Thus, stability of the antagonist-containing DP against gelling can be improved by adding an effective amount of an acid or a combination of acids (an acid or a combination of acids is also referred to herein as acid additive) and/or by using a freeze-dried antagonist of GnRH in a polymer containing dispersed phase. The acid or acid additive may be an organic acid or an inorganic acid. The acid additive preferably has a pKa of 5.0 or lower. Examples of suitable acid additives include, but are not limited to, glacial acetic acid, lactic acid, glycolic acid, glyceric acid, benzoic acid, propanoic acid, methane sulfonic acid, mesitylic acid and HCl, or a combination of these acids. For example, adding an effective amount of glacial acetic acid to the DP can improve the stability. Lactic acid can be used instead of glacial acetic acid. Lactic acid is hygroscopic and is available as 85-90% solution in water. It should be noted that the water content in the acids in larger amount may cause phase separation. Accordingly, anhydrous acids or acids containing water at less than 5% are preferred.

The amount of acid required depends to some extent on whether the antagonist was freeze-dried or not. To prepare a stable dispersed phase formulation containing a non-freeze dried GnRH antagonist, an increased amount of acid additive, e.g., greater than 20% by weight, may be needed based on the total weight of the dispersed phase. The dispersed phase composition thus obtained may not produce microspheres with low MW polymer with desired release characteristics by O/W process, and under that situation the preferred method of making microspheres may be by O/O process. On the other hand, freeze drying the antagonist can significantly minimize the amount of acid needed to dissolve the antagonist in organic solvents. The dispersed phase composition thus obtained can produce microspheres with desired release characteristics.

A clear dispersed phase may also be achieved by following an order of addition protocol regarding various components including the antagonist in the addition to the dispersed phase. One preferred order of adding various components is as follows: first, glacial acetic acid or other suitable acid is added to the antagonist to form a solution. To this solution, methanol or some other suitable solvent is added. A solvent that is typically used to dissolve a GnRH antagonist or a solvent portion in which both the antagonist and the polymer are soluble (e.g., DCM) is added to form a solution before adding any other component to this solution. Then, a portion of the DCM or other solvent that is used for dissolving the polymer in the composition is added. Preparing the antagonist in this manner may not require heating or warming at 40° C. to achieve clear solution and also it prevents initial gelling. This solution is then added to a polymer (e.g., PLGA or PLA) solution and mixed well. Alternatively, polymer solution in suitable solvent can be added to the antagonist solution in acid. This way, a clear, stable, non-gelling and filterable DP can be obtained. If any other solvent is added to the antagonist before adding and dissolving the antagonist in an acid, the resulting solution may exhibit a tendency to form a gel.

As an example, a GnRH antagonist of the present invention and other components needed to form a dispersed phase formulation having the composition, 0.984 g RG503H, 0.22 g of the novel GnRH antagonist, 0.85 g glacial acetic acid, 5.0 g DCM and 0.74 g methanol can be prepared as follows: first, a freeze-dried antagonist is dissolved in a limited amount of an acid (for example, about three times the weight of the antagonist) having a pKa of 5.0 or lower (e.g., acetic acid). Followed by that, methanol and/or a portion, preferably half, of the dichloromethane (DCM), is added to the antagonist-acid solution. The remaining DCM is used to dissolve a polymer, PLGA or PLA. The viscous polymer solution and the antagonist containing solution are mixed together to form the DP. The DP so formed may exhibit better filterability and stability against gellation than when the acid is added to the DP. Thus, to form a clear solution, the acetic acid is added first. Then by adding the methanol and/or half of DCM (2.5 g) it can form into a less viscous and clear solution. Then, the solution may be mixed with the polymer solution. A solution of GnRH antagonist of the present invention in acetic acid may also be admixed with the polymer solution directly. In an exemplary composition, the amount of each component in the composition based on weight % can be as follows: About 12.6% RG503H, about 2.8% GnRH antagonist of the present invention, about 10.9% glacial acetic acid, about 64.15% DCM and about 9.49% methanol.

Adding the components in an appropriate order is the most preferred approach to avoid stability and gelling problems. As mentioned above, as part of the order, the antagonist must first be dissolved in an acid before adding other components such as methanol to prepare a dispersed phase formulation. In this manner, dissolution of the antagonist can be achieved rapidly without any initial gelling. It can also result in a very stable solution which is easily filterable through 0.2μ filter or smaller (0.1μ, 0.05μ and so on). Thus, solubility and gelling problems can be avoided by acid addition to the DP and/or with the proper order of adding components to make the DP.

Generally, the antagonists of the present invention have improved solubility at low pH buffer levels for example. To achieve good drug incorporation efficiency, the continuous phase (CP) may be buffered to, for example, pH 7-9. The buffering capacity of CP should be high enough to neutralize the acid added to the DP formulation without dropping the pH preferably not below 6.8, certainly not below 6. This can be followed as a general method for increasing the encapsulation efficiency into microspheres. The text of the U.S. application publication 20050042294 disclosing, among other things, orntide solubility with and without acid additive in dispersed phase and methods of increasing solubility is incorporated herein by reference.

Accordingly, by practicing an aspect of the present invention, one skilled in the art can overcome problems associated with the use of high levels GnRH antagonists in a formulation. Such formulations can be used to produce microspheres with consistent release characteristics. Further, such formulations can be filtered using micro filters, and one would be able to obtain filter sterilizable GnRH antagonist containing formulations for use in the manufacture of microspheres. For example, the solutions prepared according to the present invention can be filtered using a 0.2μ filter. Both PLA or PLGA microspheres can be prepared to achieve a 3 month, 6 month or 1 year release formulations.

In another aspect of the invention, GnRH antagonist peptides are also used for diagnostic purposes. In vitro tests can be carried out to determine whether certain tumor cells are sensitive to GnRH. For example, in an in vitro assay, tumor cell cultures are treated with a given GnRH antagonist and then the cultures are monitored for hormonal secretions and cell proliferation. Likewise, these peptides can be injected in vivo to determine its effect on gonadotropin or steroid secretions. For example, blood samples of a patient is assayed to determine the extent of decrease of hormonal secretion, e.g. LH secretion.

GnRH antagonists of the present invention can be synthesized in large quantities by peptide synthesis methods known in the art.

EXAMPLES

The following examples further illustrates the present invention, but of course, should not be construed as in any way limiting its scope. The examples below were carried out using conventional techniques that are well known and routine to those of skill in the art, except where otherwise described in detail. A GnRH antagonist having a chemical structure shown in FIG. 1 has been used, which has also been referred to herein as "novel GnRH antagonist," in the working examples described below.

1. Water Solubility of GnRH Antagonist Having a Chemical Structure Shown in FIG. 1

The novel GnRH antagonist was synthesized by Bachem California, Inc., Torrence, Calif. This acetate salt of the compound was an acetate salt, a white powder with the peptide purity of >98%, and it is different from orntide acetate by having nicotinoyllysine instead of picolinoyllysine in position 5.

Solubility of the novel GnRH antagonist was compared with that of orntide acetate at room temperature. In this experiment, 50 mg of the novel GnRH antagonist was weighed into a small glass container and 2 mL of purified water was added to it. It was found to dissolve in less than 30 seconds, with relatively gentle mixing. An additional 3 mL of water was added, the solution mixed, and the pH was determined: 5.4. The same procedure was used to test the solubility of orntide acetate (known in the art as ornirelix). The final concentration of 10 mg/mL was found to be approximately twice that of what the present inventors could achieve with orntide acetate.

Separately, another 50 mg aliquot was weighed out and 1 ml of water was added. This also dissolved. This is 50 mg/mL in concentration, which is 10 times what is possible to dissolve with orntide acetate. Thus, the water solubility of the novel GnRH antagonist was found to be surprisingly good.

2. In Vivo Administration of One Embodiment of the Instant GnRH Antagonist

To demonstrate pharmacological efficacy of the novel GnRH antagonist in suppressing testosterone in vivo, an art recognized standard experimental rat model was used. Briefly, male Sprague Dawley rats weighing approximately 300 g were purchased from Harlan (Indianapolis, Ind.) and used immediately after the quarantine period required by a University of Kentucky Animal Research Facility approved protocol.

The evaluation was conducted in two groups of rats. Group 1 included 6 rats to be administered with the novel GnRH antagonist. The other group was a control group consisting of 2 rats. The novel GnRH antagonist was administered subcutaneously (scapulae). Blood samples (1 mL) for testosterone level determinations were collected from the tail vein at 0, 1, 3, 6, 12, 24, and 48 hours. Serum was extracted by centrifugation at 2000 rpm for 15 min and stored at −20 C until determination of testosterone/LH levels. Rat plasma testosterone was determined using Active™ Testosterone RIA DSL-4000 kits purchased from Diagnostic Systems, Inc. Webster, Tex. To effect a sufficient washout period the doses were administered at weekly intervals. Table 1 shows the injection schedule, peptide mass and dilution requirements, and injection volume for the novel GnRH antagonist administration.

Table 1 shows the protocol for the novel GnRH antagonist administration. A total of six rats were used for each dose tested. In the first week, each rat received a single dose of 15 µg. In the second week, the dose increased to 30 µg. Next, in the third week, each rat received a single dose of 60 µg. Table 2 is the control rat group with a total of 2 rats that received only vehicle.

TABLE 1

Administration of the novel GnRH antagonist

| Week | Dose Required | Mass Amount Required | Amount of Drug Source Required | Dilution of Stock | Injection Volume per rat |
|---|---|---|---|---|---|
| 1st week | 15 µg/rat | 15 µg × 6 = 90 µg | 2 mg | 2 mg + 40 mL WFI (50 µg/mL) | 0.3 mL containing 15 µg |
| 2nd week | 30 µg/rat | 30 µg × 6 = 180 µg | 2 mg | 2 mg + 20 mL WFI (100 µg/mL) | 0.3 mL containing 30 µg |
| 3rd week | 60 µg/rat | 60 µg × 6 = 360 µg | 2 mg | 2 mg + 10 mL WFI (200 µg/mL) | 0.3 mL containing 60 µg |

TABLE 2

Vehicle Control (two rats per week)

| Week | Injection Volume of WFI |
|---|---|
| 1st week | 0.3 Ml |
| 2nd week | 0.3 Ml |
| 3rd week | 0.3 Ml |

Figure 2:
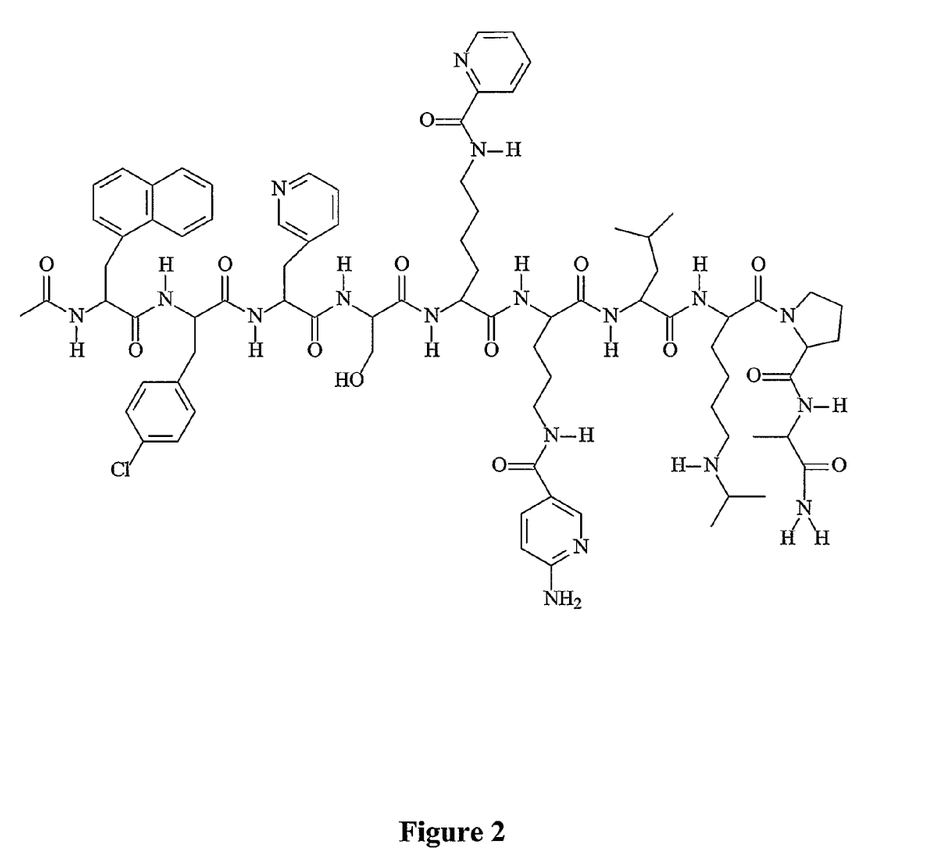
FIG. 2 shows mean serum testosterone levels in rats after the GnRH antagonist (AcDNal$^1$, DpClPhe$^2$, D3Pal$^3$ Ser$^4$, NicLys$^5$, D(6ANic)Orn$^6$, Leu$^7$, IprLys$^8$, Pro$^9$, DAla$^{10}$NH$_2$) administration for three weeks. Testosterone levels after the administration of analog having a chemical structure shown in FIG. 1 at a dose of 15 µg/rat in week 1 (2A), 30 µg/rat in week 2 (2B) and 60 µg/rat in week 3 (2C).
Figure 2A:
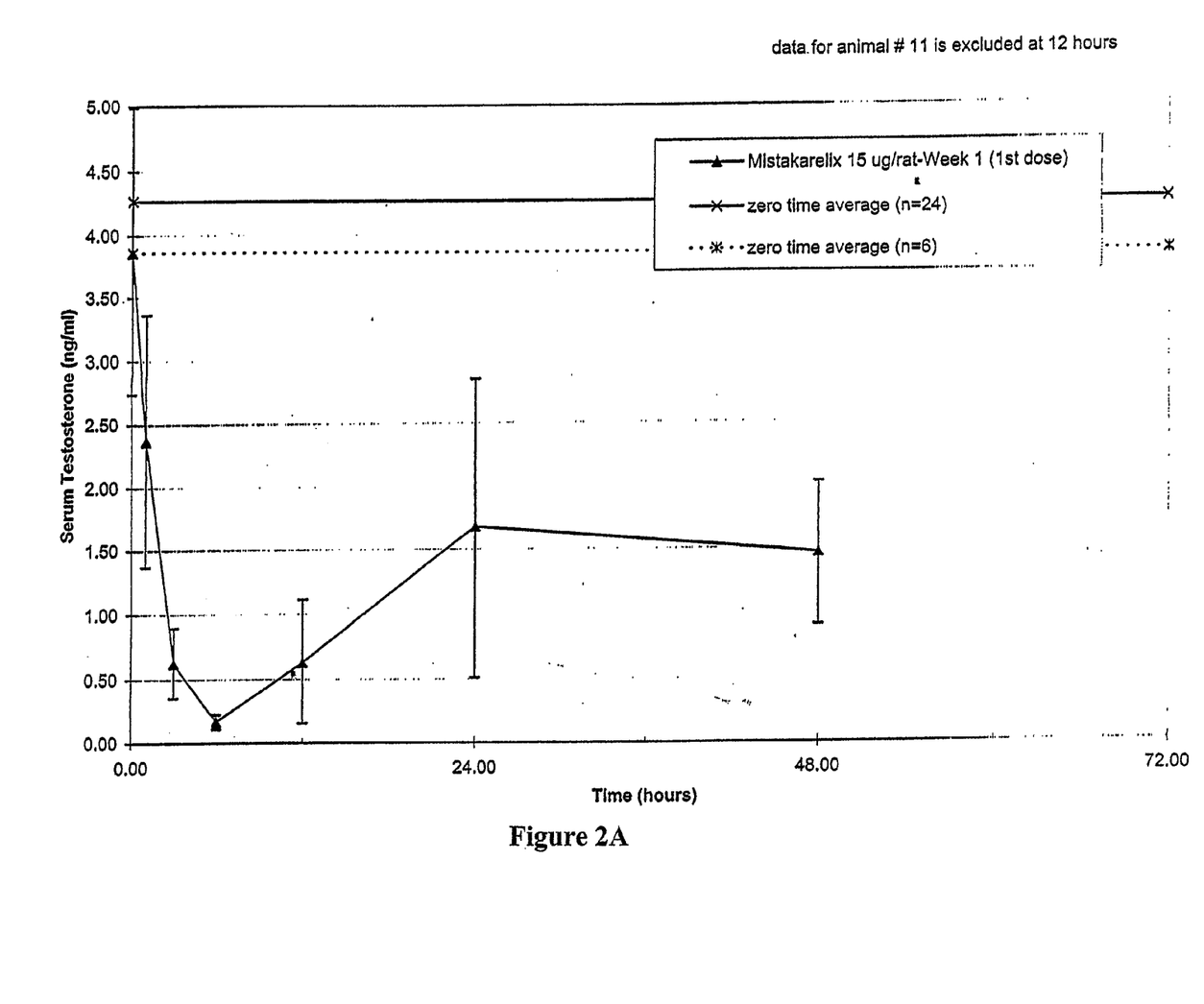
Figure 2B:
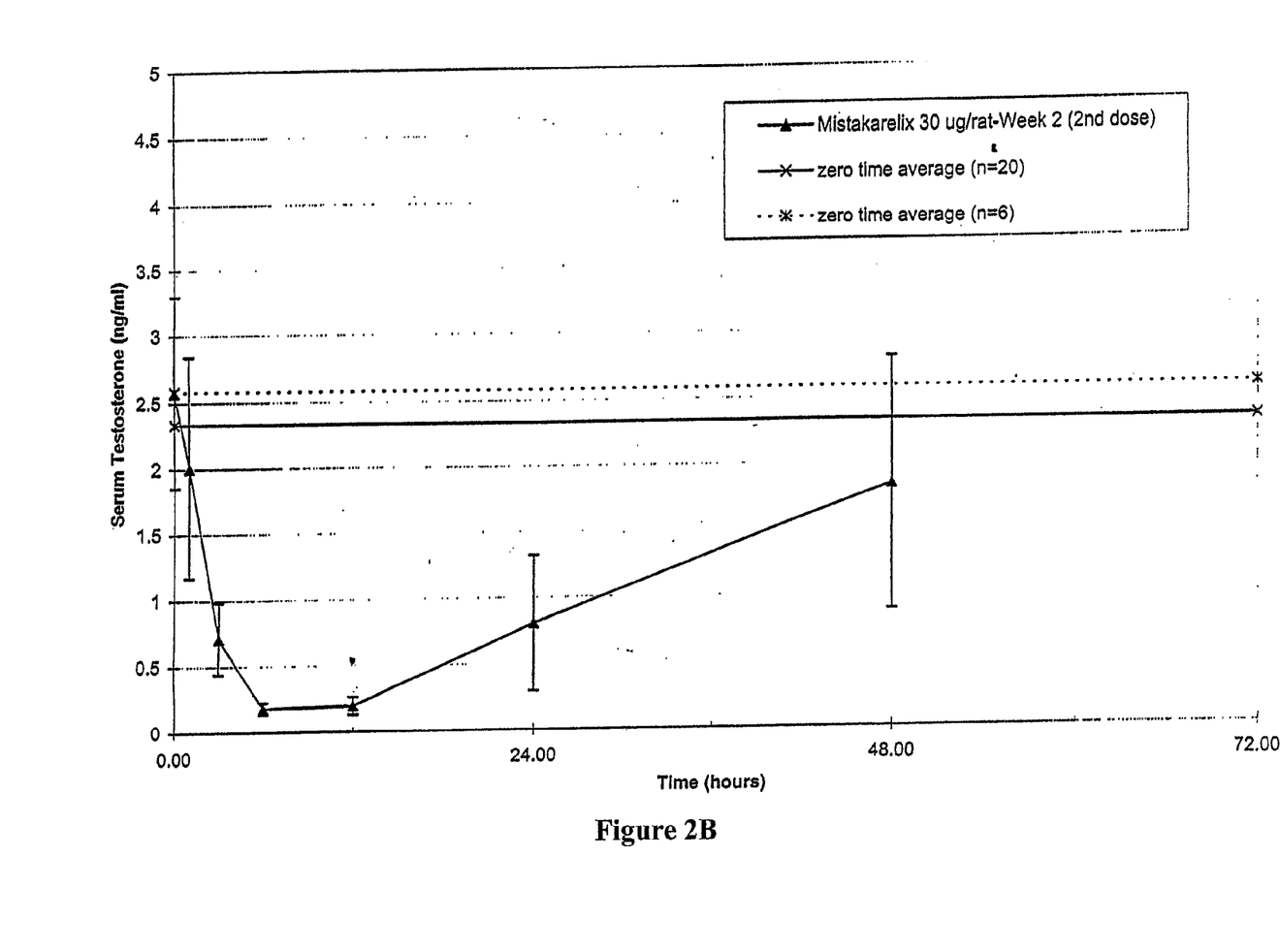
Figure 2C:
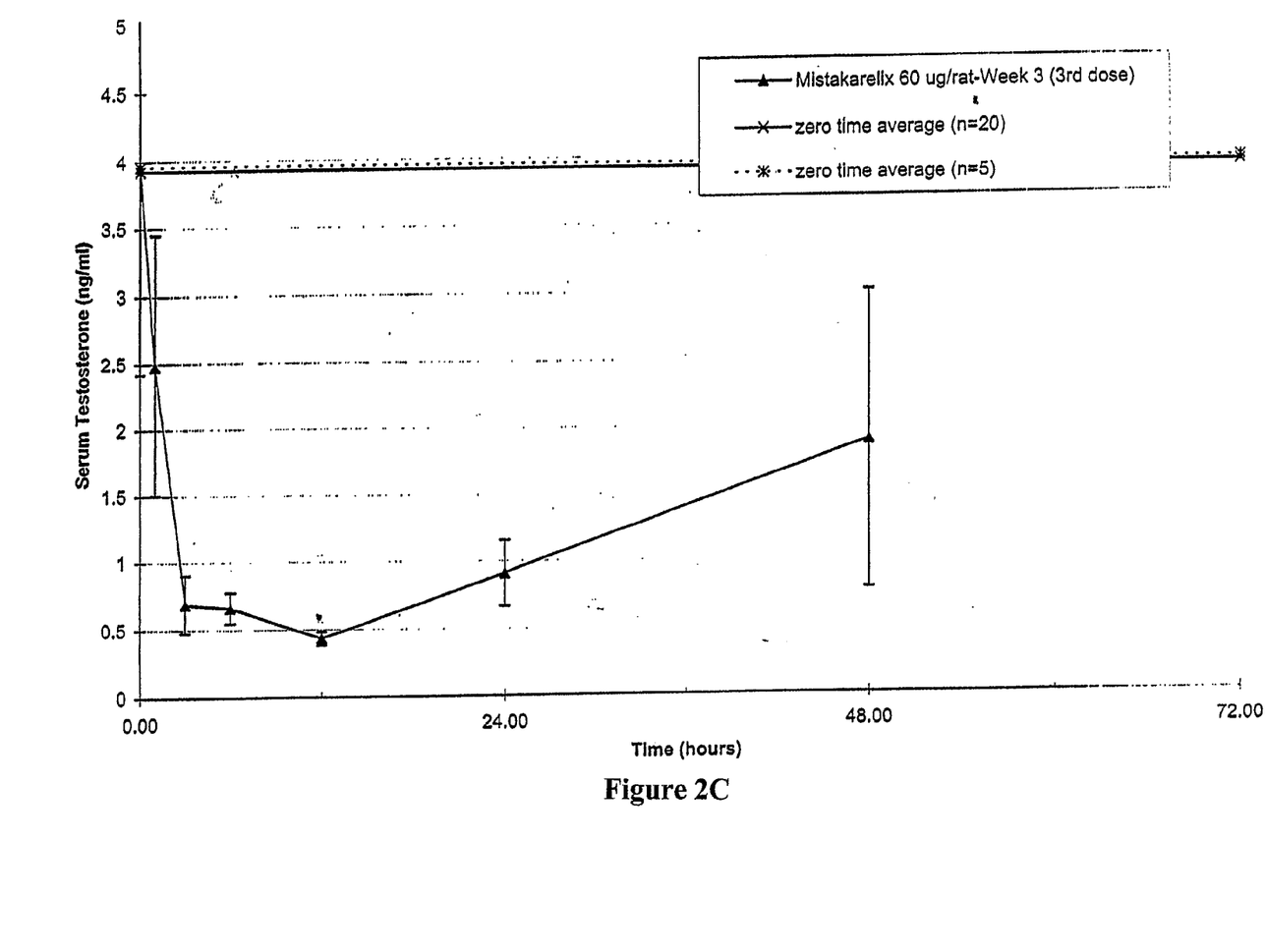
Figure 3A:
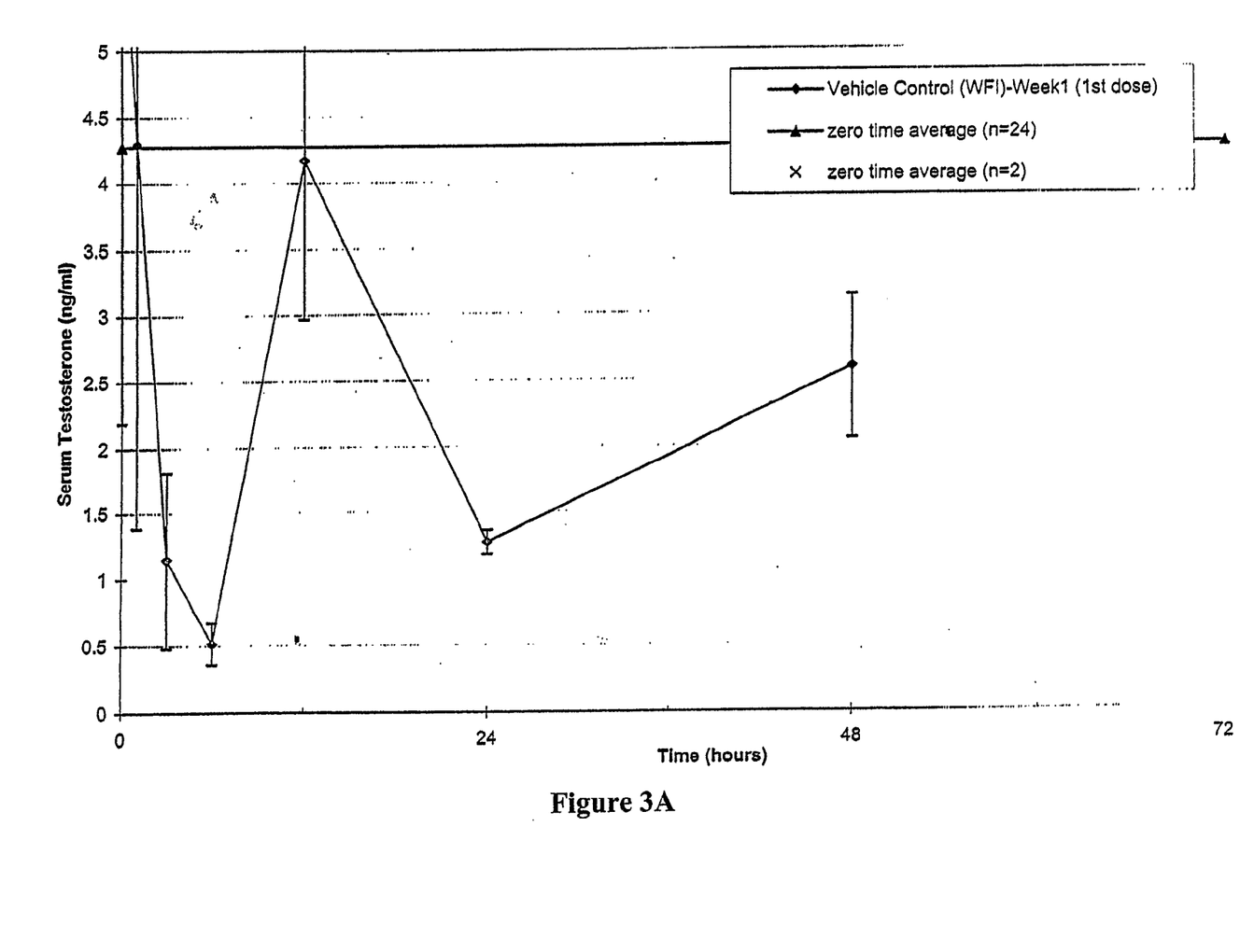
Figure 3B:
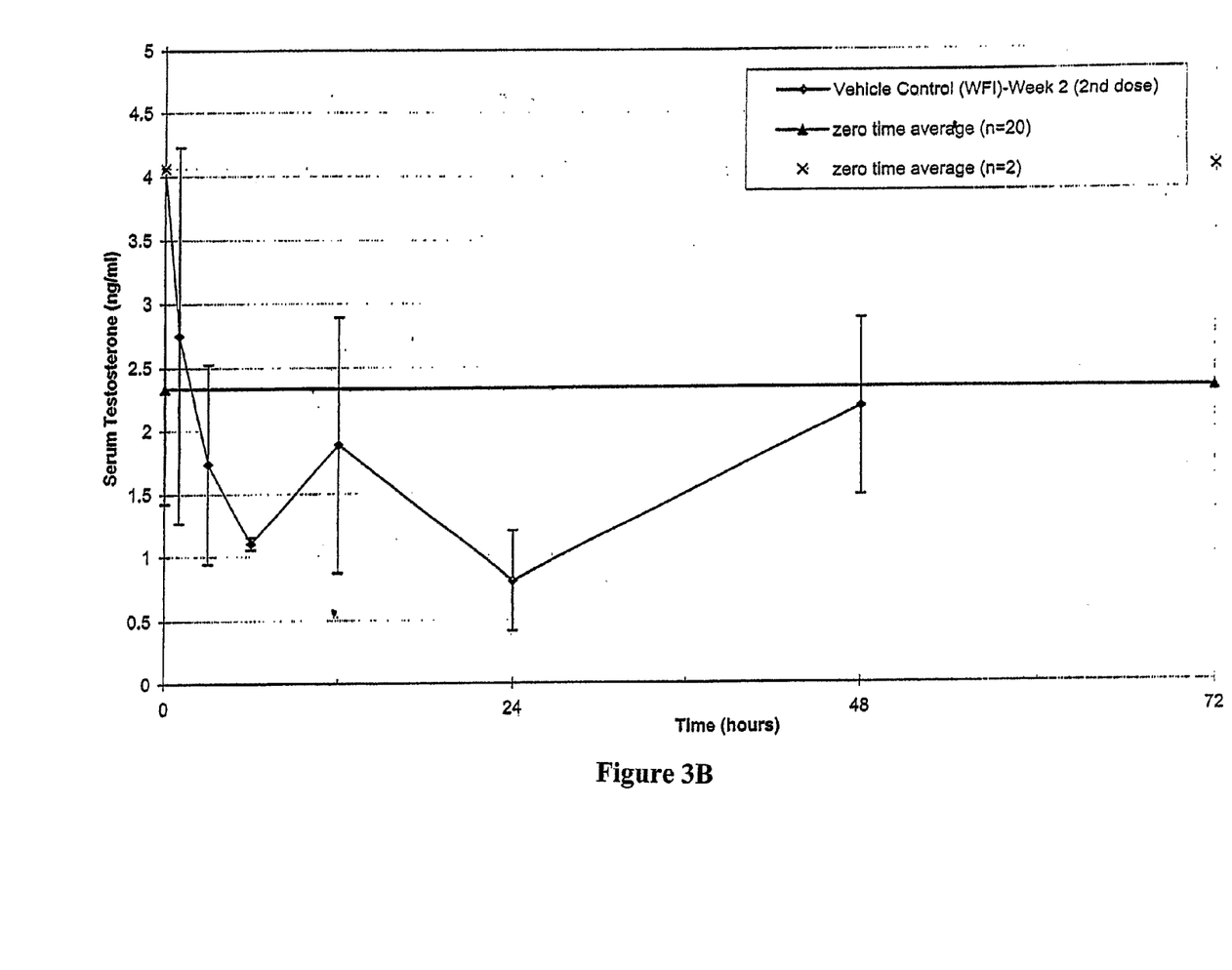
Figure 3C:
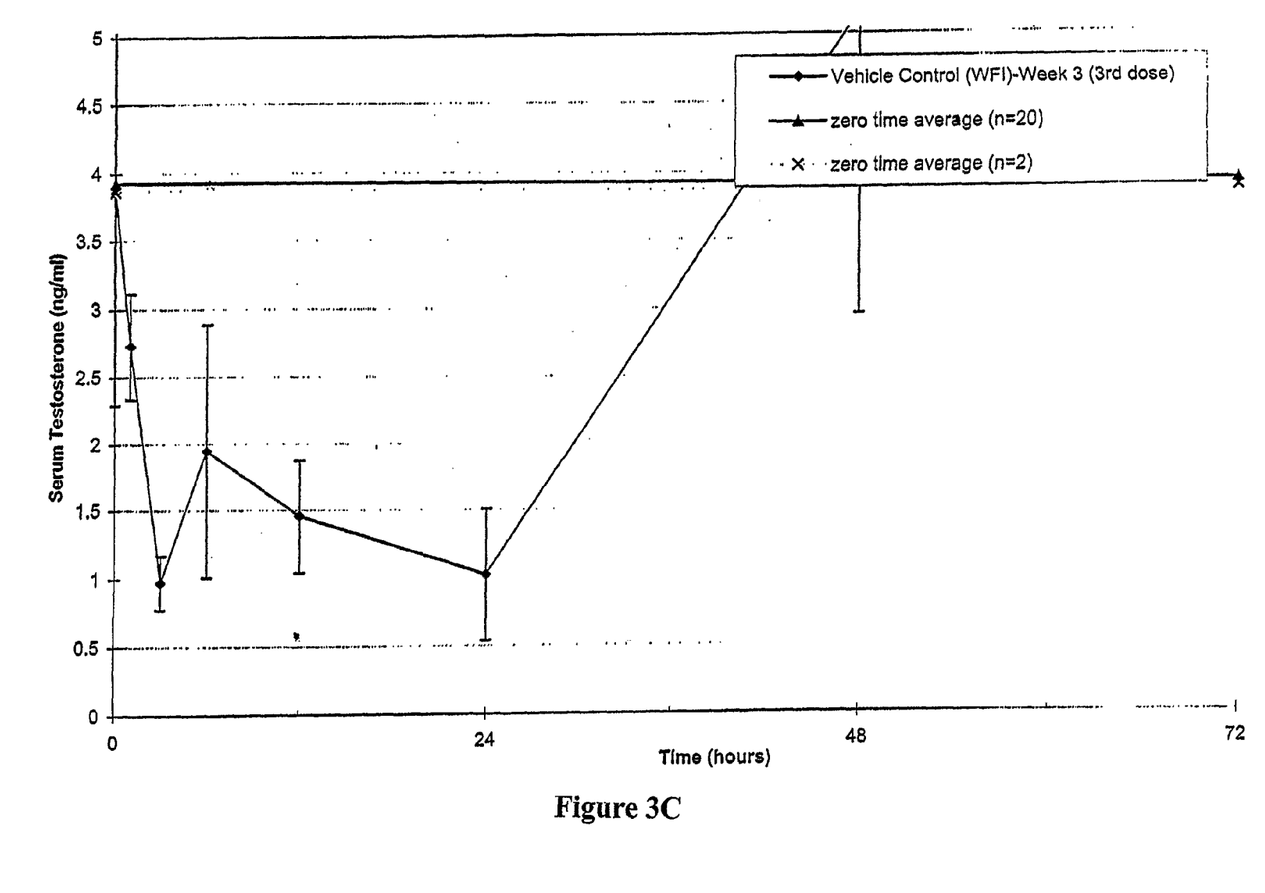

FIGS. 2A-2C show the result for the first three weeks of the novel GnRH antagonist administration. As shown in FIG. 2A, when the rats were administered with 15 µg of the novel GnRH antagonist per rat, suppression was seen at 6 hours where testosterone levels reached 0.2 ng/mL (means SD). Chemical castration of testosterone (i.e. ≦0.5 ng/ml) persisted for about 12 hours after which testosterone levels began to climb to 1.5 ng/ml.

When the rats were administered with 30 µg of the novel GnRH antagonist per rat, suppression lasted for at least 12 hours and by 24 hours, testosterone levels were greater than 0.5 ng/mL. See FIG. 2B. The data from the 60 µg dose as shown in FIG. 2C demonstrates similar results as seen with 30 µg dose.

The previous description of the preferred embodiments is provided to enable any person skilled in the art to make and use the present invention. The various modifications to these embodiments will be readily apparent to those skilled in the art, and the generic principles defined herein may be applied to other embodiments without the use of the inventive faculty. Thus, the present invention is not intended to be limited to the embodiments shown herein but is to be accorded the widest scope consistent with the principles and novel features disclosed herein.

What is claimed is:

1. A gonadotropin releasing hormone antagonist having the formula:

AcDNal$^1$, DpClPhe$^2$, D3Pal$^3$ Ser$^4$, NicLys$^5$, D(6ANic) Orn$^6$, Pro$^9$, DAla$^{10}$NH$_2$.

2. A gonadotropin releasing hormone antagonist having the formula:

AcDNal$^1$, DpClPhe$^2$, D3Pal$^3$ Ser$^4$, NicLys$^5$, D(6ANic)Orn$^6$, Leu$^7$, IprLys$^8$, Pro$^9$, DAla$^{10}$NH$_2$.

3. A pharmaceutical composition comprising the antagonist of claim 2 and a pharmaceutically acceptable carrier or diluent.

4. A method of suppressing testosterone levels in a mammal comprising administering to the mammal the antagonist or composition as in any of the preceding claims in an amount sufficient to achieve suppression of said levels in the mammal compared to an untreated mammal.

5. The method of claim 4, wherein the antagonist or composition is administered subcutaneously.

6. The method of claim 4, wherein the mammal is a human.

7. A method for antagonizing gonadotropin releasing hormone in a mammal suffering from said hormone related disorder comprising administering an effective amount of a composition comprising a GnRH antagonist to the mammal, wherein said antagonist is AcDNal$^1$, DpClPhe$^2$, D3Pal$^3$ Ser$^4$, NicLys$^5$, D(6ANic)Orn$^6$, Leu$^7$, IprLys$^8$, Pro$^9$, DAla$^{10}$NH$_2$.

8. The method of claim 7, wherein said disorder is a testosterone dependent disorder, benign prostate hypertrophy or prostate cancer.

9. The method of claim 7, wherein said composition is administered subcutaneously.

10. The method of claim 6, wherein said mammal is a human.

11. A method for reversible suppression of male fertility comprising treating a male with an effective amount of a composition comprising a GnRH antagonist to the mammal, wherein said antagonist is AcDNal$^1$, DpClPhe$^2$, D3Pal$^3$ Ser$^4$, NicLys$^5$, D(6ANic)Orn$^6$, Leu$^7$, IprLys$^8$, Pro$^9$, DAla$^{10}$NH$_2$, wherein male fertility is restored after cessation of treatment with said antagonist.

12. The method of claim 10, wherein the amount of antagonist in the composition is from about 0.09 to 2.5 mg per kilogram of body weight per day.

13. The method of claim 11, wherein the amount of antagonist in the composition is about 0.09 mg per kilogram of body weight per day.

14. A composition for a dispersed phase formulation comprising a gonadotropin releasing hormone (GnRH) antagonist having the formula: AcDNal$^1$, DpClPhe$^2$, D3Pal$^3$ Ser$^4$, NicLys$^5$, D(6ANic)Orn$^6$, Leu$^7$, IprLys$^8$, Pro$^9$, DAla$^{10}$NH$_2$, and an acid additive consisting of one or more acids having a pKa of 5.0 or lower.

15. The composition of claim 14, wherein the GnRH analog is a freeze-dried GnRH antagonist.

16. The composition of claim 14, wherein the acid additive is an organic or an inorganic acid additive or a combination thereof.

17. The composition of claim 16, wherein the organic or inorganic acid additive is one acid.

18. The composition of claim 17, wherein the organic acid additive is selected from the group consisting of: glacial acetic acid, lactic acid, glycolic acid, glyceric acid, benzoic acid, propanoic acid, methane sulfonic acid, and mesitylic acid or a combination of these acids.

19. The composition of claim 17, wherein the inorganic acid additive is HCl.

20. The composition of claim 14, wherein the composition further comprises a biocompatible and biodegradable polymer.

21. The dispersed phase formulation of claim 14, wherein the polymer is a homopolymer of lactic acid or a copolymer of lactic acid and glycolic acid.

* * * * *